United States Patent [19]

Croll

[11] Patent Number: 4,662,842

[45] Date of Patent: May 5, 1987

[54] FINGER-MOUNTED LIGHT FILTER

[76] Inventor: Theodore P. Croll, 685 South Chubb Dr., Doylestown, Pa. 18901

[21] Appl. No.: 766,261

[22] Filed: Aug. 16, 1985

[51] Int. Cl.[4] ................................................. A61C 3/00
[52] U.S. Cl. ..................................... 433/141; 350/1.1; 350/318; 433/229
[58] Field of Search ................. 433/229, 141; 350/1.1, 350/98, 248, 318, 638; 351/44, 45, 46, 47, 48, 49; 63/1 R

[56] References Cited

U.S. PATENT DOCUMENTS 1,536,365  5/1925  Wiseman .............................. 350/248
3,104,176  9/1963  Hovey .................................. 350/311

Primary Examiner—John J. Wilson
Assistant Examiner—Adriene J. Lepiane
Attorney, Agent, or Firm—Gregory J. Gore

[57] ABSTRACT

A hand-mounted light shield for dentists is disclosed which provides eye protection against harmful light-curing guns used in resin bonding. A substantially circular finger disc is provided with finger ring element for attachment to the hand. The finger mounting ring permits the filter to be maintained in a ready-to-use position while permitting the free use of both hands.

4 Claims, 2 Drawing Figures

FINGER-MOUNTED LIGHT FILTER

FIELD OF INVENTION

This invention relates generally to eye protection for dentists. This invention is a light filtering device employed to protect the physician's eyes from damaging light rays emitted from the curing light used in resin bonding.

BACKGROUND OF THE INVENTION

The advent of modern resin-bonding materials in dentistry has brought with it problems of eye protection for the dentist and his assistants. The need for suitable eye protection is explained in detail in my co-pending application, Ser. No. 723,332, for a Hand-Held Light Shield which has a similar purpose to my present invention enclosed herein.

Prior art examples of light filters used in dentistry for this purpose, including my previous design presented in my co-pending application, require the assistance of either the patient or a physician's assistant to hold the light shield. The need, therefore, has arisen for a light shield which can be effectively used by a sole practioner without any additional assistance.

OBJECTS AND SUMMARY OF THE INVENTION

In order to solve the problem of providing a light-protective device for a dentist which may be used without the assistance of another, the present device has been invented with the following objects in mind. First, to provide a hand-mounted light shield which is convenient to use and which does not impede the use of both of the physician's hands during the resin-cured bonding process. Secondly, it's an object of the instant invention to devise a light shield which is simple and inexpensive to manufacture.

The foregoing objects are achieved by the design of a simple circular disc, made of material which filters out the harmful light rays in the 400–525 nanometer range which have been shown to be a harmful by-product of the resin-curing light guns used in modern dental resin bonding. The circular disc is complimented by a finger ring attachment so that the disc may be secured to the physician's hand around his finger, yet not impede the dexterity or use of the hand on which the light shield is mounted. When in use, the filter disc is held securely between the thumb and the first finger in the web of the hand while the other fingers of that hand may be used to retract the lips of the patient in order to expose the tooth which is being operated upon. Additionally, when the physician needs both hands free for other preparations, the filter disc can be flipped over the back portion of the physician's hand while still connected by the finger ring so that the physician then retains the use of all five fingers on that hand. In order that one design may accommodate many different hand sizes, a series of holes are provided in the filter disc at different distances from the circumference. One size finger ring can be adjusted to the individual physician's hand simply by mounting the finger ring in a mounting hole which provides the proper spacing between the circumference of the disc and the point of the finger ring farthest from the disc.

DESCRIPTION OF THE PREFERRED EMBODIMENT

Figure 1:
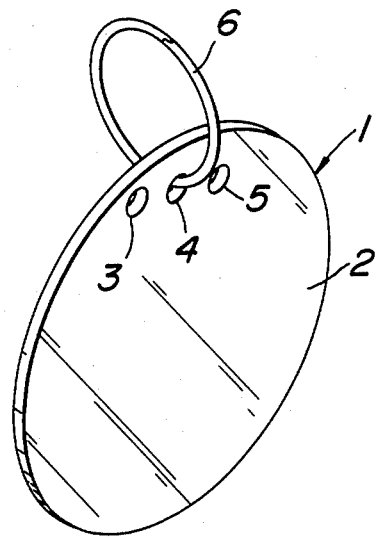
FIG. 1 shows an isometric view of the instant invention.
Figure 2:
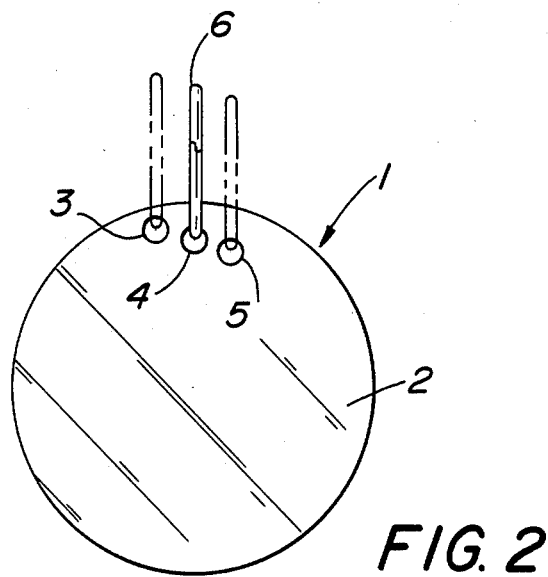
FIG. 2 shows the front view of the instant invention showing three (3) different possible positions for the finger ring.

The main filter disc 1 is made of plastic of the type sold by Rohm & Haas Company under the trade name PlexiGlas G (R)-orange. The material is shown to adequately filter out harmful light rays emitted by the light curing guns used in the dental resin-bonding process. This disc is basically circular in configuration and about $2\frac{1}{2}$–3 inches in diameter. A circular finger ring element 6 is attached to the main filter disc through one of several mounting holes 3, 4 or 5. These mounting holes are spaced different distances from the outer circumferential edge Number 1 of the filter disc. This mounting arrangement allows for different spacing within the finger ring so that a comfortable fit for one size ring may be achieved for different sized fingers. The finger ring may be a simple steel loop of the type commonly used for a key ring.

OPERATION

In use, the light filter disc is worn on the physician's index finger through the finger ring element 6. The disc remains against the back of the physician's hand except when in use. This at-ready position allows the physician the full use of all fingers of the hand on which the filter disc is worn. At the moment when the light-curing phase of the resin-bonding process begins, the physician simply flips the filter disc over into the front of his hand and holds the filter disc securely in the web of his hand between the forefinger and thumb. In this way, the remaining three (3) fingers of this hand are free to be used for positioning the patient's lips away from the tooth being operated upon or other desired manipulation of that hand. As successive curing treatments may be performed, the filter disc is conveniently flipped from front to back of the hand as described above in a manner which makes this filter extremely convenient to use and which allows the physician to keep both hands unencumbered for other aspects of treating the patient. In this way, no assistance is required from the patient or a physician's helper so that a sole practitioner may use a hand-held light shield easily and conveniently.

It should be understood that there may be modifications and adaptations of the specific embodiment of the present invention described herein and still fall within the scope and spirit of the invention. It is therefore intended that the scope of the invention be determined by the appended claims and their legal equivalents.

What is claimed is:

1. A light shield device used in dentistry for eye protection to be worn on the hand comprising:
    (a) a transparent light filtering disc having the property of filtering out light wavelengths in the 400–525 nanometer range and
    (b) a finger ring slideably attached to said filter disc through a hole in said disc near the circumference thereof for attaching said disc to the hand of the user.

2. The light shield device of claim 1 wherein said disc is provided with plurality of holes therethrough at different distances from the circumference thereof for alternate mounting of said finger ring.

3. The light shield device of claim 2 further described in that said light filtering disc is substantially circular.

4. The light shield device of claim 3 wherein said filter disc is made of plastic.

* * * * *